United States Patent
Blumenkranz et al.

(10) Patent No.: US 6,246,200 B1
(45) Date of Patent: Jun. 12, 2001

(54) MANIPULATOR POSITIONING LINKAGE FOR ROBOTIC SURGERY

(75) Inventors: Steven J. Blumenkranz, Redwood City; David J. Rosa, San Jose, both of CA (US)

(73) Assignee: Intuitive Surgical, Inc., Mountain View, CA (US)

(*) Notice: Subject to any disclaimer, the term of this patent is extended or adjusted under 35 U.S.C. 154(b) by 0 days.

(21) Appl. No.: 09/368,309

(22) Filed: Aug. 3, 1999

Related U.S. Application Data

(60) Provisional application No. 60/095,303, filed on Aug. 4, 1998.

(51) Int. Cl.⁷ .............................. B25J 9/18; G05B 19/19
(52) U.S. Cl. .............................. 318/568.11; 318/568.12; 318/568.21; 318/568.25; 901/1; 901/15; 901/30; 128/DIG. 7; 600/117
(58) Field of Search .................. 318/568.11, 568.12, 318/568.16, 568.19, 568.21, 568.25; 901/1, 2, 15, 16, 28, 30, 41, 46; 128/DIG. 7, DIG. 26, 897, 898, 899; 600/117; 601/1

(56) References Cited

U.S. PATENT DOCUMENTS

| | | |
|---|---|---|
| 5,050,608 | 9/1991 | Watanabe et al. . |
| 5,078,140 | 1/1992 | Kwoh . |
| 5,184,601 | 2/1993 | Putman . |
| 5,269,305 | 12/1993 | Corol . |
| 5,279,309 | 1/1994 | Taylor et al. . |
| 5,343,385 | 8/1994 | Joskowics et al. . |
| 5,351,676 | 10/1994 | Putman . |
| 5,378,968 * | 1/1995 | Ezawa et al. ............... 318/568.1 |
| 5,397,323 | 3/1995 | Taylor et al. . |
| 5,417,210 | 5/1995 | Funda et al. . |
| 5,441,042 | 8/1995 | Putman . |
| 5,441,505 | 8/1995 | Nakamura . |
| 5,445,166 | 8/1995 | Taylor . |
| 5,494,034 | 2/1996 | Schlondorff et al. . |
| 5,597,146 | 1/1997 | Putman . |
| 5,631,973 | 5/1997 | Green . |
| 5,649,956 | 7/1997 | Jensen et al. . |

(List continued on next page.)

FOREIGN PATENT DOCUMENTS

| | | |
|---|---|---|
| WO 95/01757 | 1/1995 | (WO) . |
| WO 99/50721 | 10/1999 | (WO) . |

OTHER PUBLICATIONS

Alexander Arthur D., III, "Impacts of telemation on modern society" *On Theory and Practice of Robots and Manipulators*, vol. II (1974) Springer–Verlag, New York, pp. 121–136.

*Primary Examiner*—Robert E. Nappi
*Assistant Examiner*—Edgardo San Martin
(74) *Attorney, Agent, or Firm*—Townsend Townsend & Crew LLP; Mark D. Barrish, Esq.

(57) ABSTRACT

Techniques and structures are provided for aligning robotic elements with an internal surgical site and each other. Manually positionable linkages support surgical instruments. These linkages maintain a fixed configuration until a brake system is released. While the brake is held in a released mode, the linkage allows the operating room personnel to manually move the linkage into alignment with the surgical site. Joints of the linkage translate the surgical instrument in three dimensions, and orient the surgical instrument about three axes of rotation. Sensors coupled to the joints allow a processor to perform coordinate transformations that can align displayed movements of robotically actuated surgical end effectors with a surgeon's hand inputs at a control station.

31 Claims, 14 Drawing Sheets

U.S. PATENT DOCUMENTS

| | | |
|---|---|---|
| 5,696,837 | 12/1997 | Green . |
| 5,697,939 | 12/1997 | Kubota et al. . |
| 5,737,500 * | 4/1998 | Seraji et al. ............................ 395/86 |
| 5,748,767 | 5/1998 | Raab . |
| 5,762,458 | 6/1998 | Wang et al. . |
| 5,784,542 * | 7/1998 | Ohm et al. ............................. 395/95 |
| 5,792,135 * | 8/1998 | Madhani et al. ......................... 606/1 |
| 5,800,423 | 9/1998 | Jensen . |
| 5,807,378 * | 9/1998 | Jensen et al. ............................ 606/1 |
| 5,808,665 | 9/1998 | Green . |
| 5,817,084 | 10/1998 | Jensen . |
| 5,855,583 | 1/1999 | Wang et al. . |
| 5,876,325 * | 3/1999 | Mizuno et al. ...................... 600/102 |

* cited by examiner

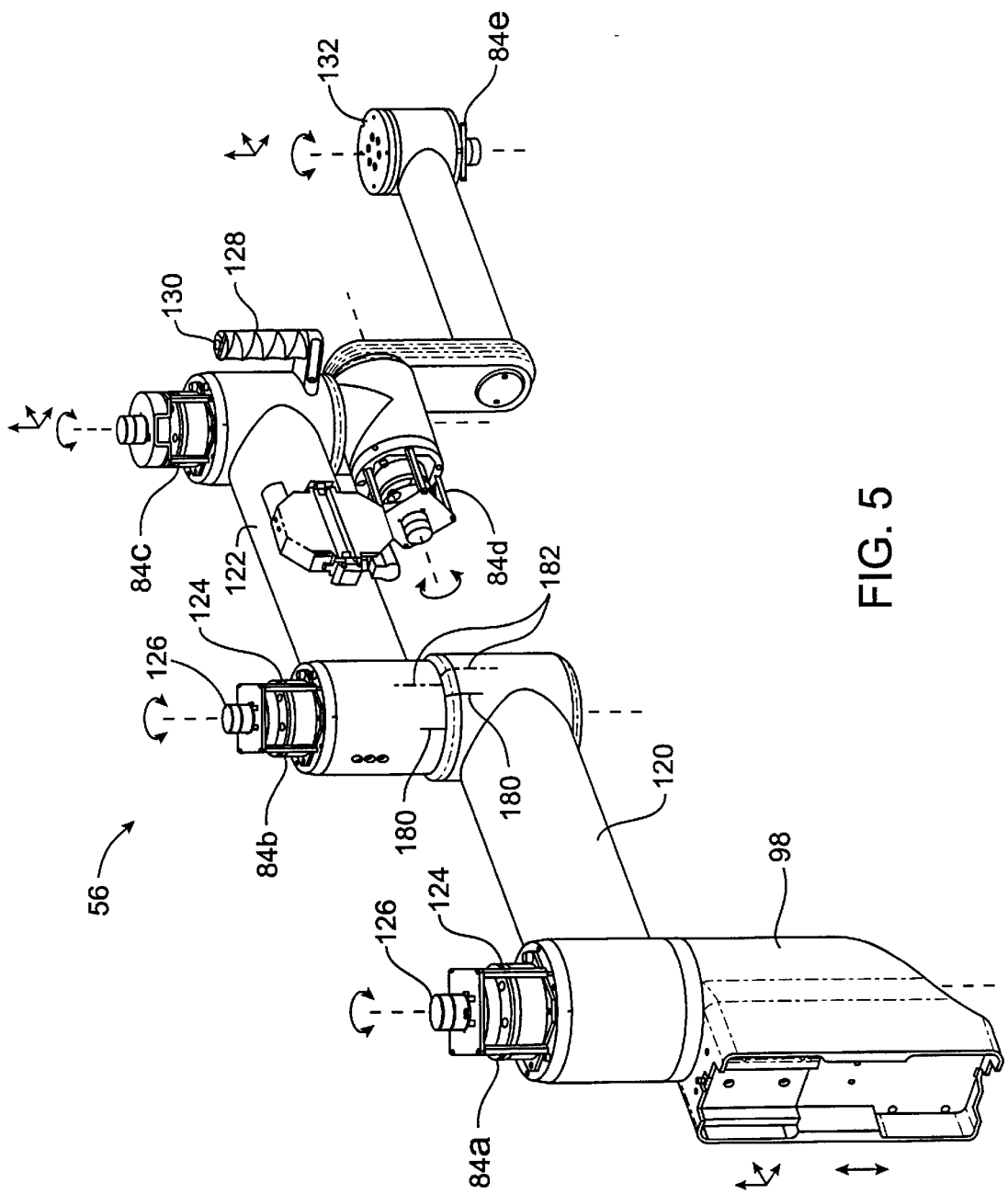

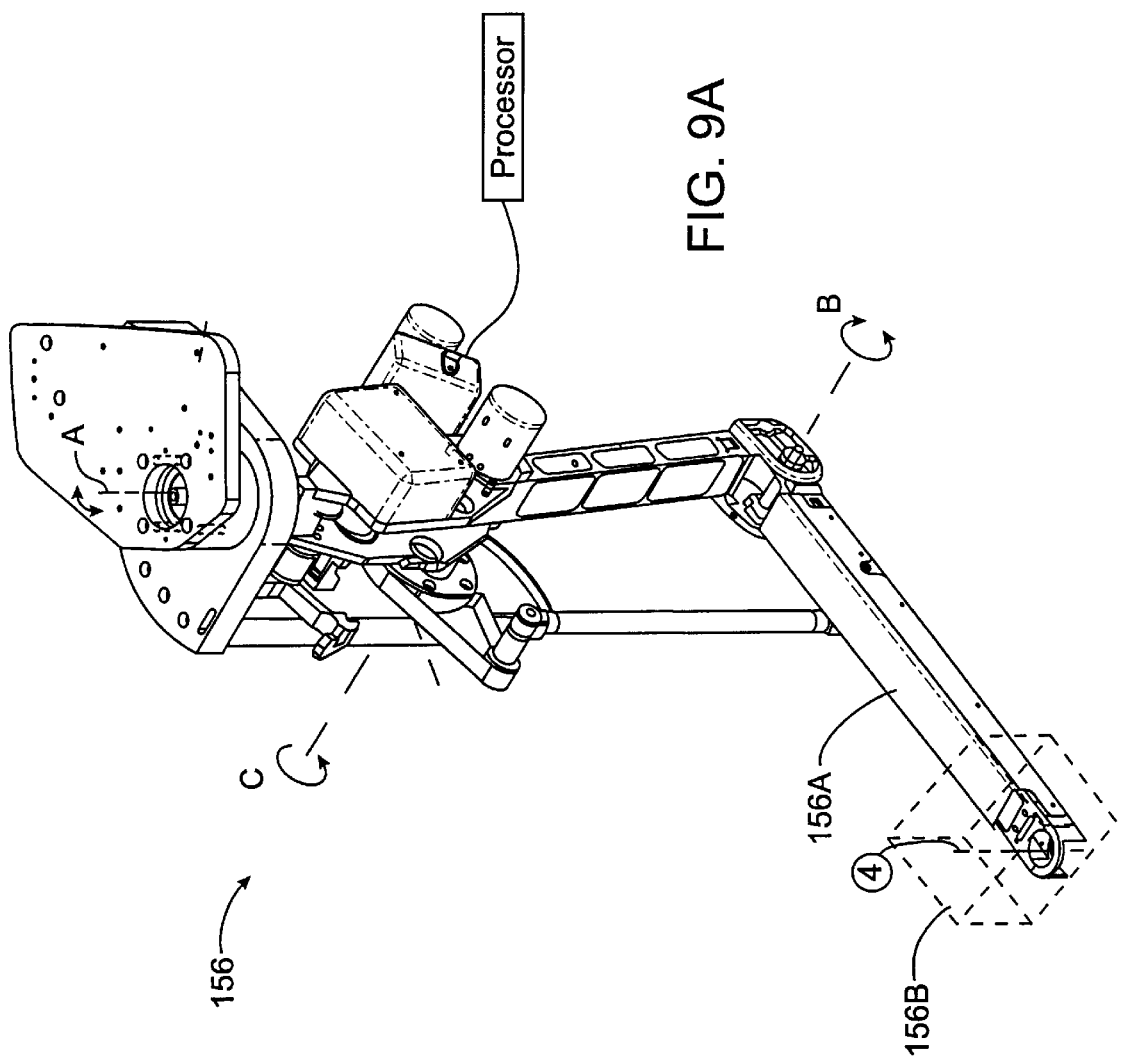

MANIPULATOR POSITIONING LINKAGE FOR ROBOTIC SURGERY

CROSS-REFERENCES TO RELATED APPLICATIONS

This application claims the benefit of priority from (provisional) application No. 60/095,303, filed on Aug. 4, 1998, the full disclosure of which is incorporated herein by reference.

BACKGROUND OF THE INVENTION

This invention generally relates to surgical devices, systems, and methods, and more particularly provides structures and techniques for manually aligning a robotic surgery system with a desired surgical site.

In robotically assisted or telerobotic surgery, a surgeon typically operates a master controller to control the motion of surgical instruments at the surgical site. The controller may be separated from the patient by a significant distance (e.g., across the operating room, in a different room, or in a completely different building than the patient). Alternatively, a controller may be positioned quite near the patient in the operating room. Regardless, the controller will typically include one or more hand input devices (such as joysticks, exoskeletal gloves, or the like) which are coupled by a servomechanism to a surgical instrument. More specifically, servo motors articulate the surgical instrument based on the surgeon's manipulation of the hand input devices. During an operation, the surgeon may employ, via the robotic surgery system, a variety of surgical instruments, such as tissue graspers, needle drivers, electrosurgical cautery probes, etc. Each of these structures perform functions for the surgeon, for example, holding or driving a needle, grasping a blood vessel, or dissecting, cauterizing, or coagulating tissue.

A variety of structural arrangements might be used to support the surgical instrument at the surgical site during robotic surgery. It has previously been proposed to support the surgical instrument with a mechanical linkage that is driven by the servomotors so that movement of the hand input devices at the master controller causes the surgical instrument to move in a corresponding manner at the surgical site. The driven linkage or "slave" is often called a robotic surgical manipulator.

Robotic surgery has potential applications for a wide variety of surgical procedures and settings. Patients may benefit from robotic surgery directed by a surgeon who is at a considerable distance from the patient. This may allow treatment of soldiers in a battlefield environment, or treatment of trauma victims at considerable distances from a skilled surgical staff. Of particular importance to the present invention, robotic surgery also may provide significant benefits for performing minimally invasive surgical procedures located near the surgeon, but which are best performed within internal surgical sites which are difficult and/or impossible to access directly using a surgeon's hands.

In traditional minimally invasive surgery, elongate surgical instruments are introduced to an internal surgical site, often through trocar sleeves or cannulas. The surgical site often comprises a body cavity, such as the patient's abdomen. The body cavity may optionally be distended using a clear fluid such as an insufflation gas. Such minimally invasive procedures are often performed under the direction of a surgical imaging system, typically by introducing an endoscope to the surgical site. In traditional minimally invasive surgery, the surgeon then manipulates the tissues using end effectors of the elongate surgical instruments by actuating the instrument's handles while viewing the surgical site on a video monitor.

Robotically assisted minimally invasive surgery instead makes use of a servomechanism to actuate the surgical end effectors of the instruments. This allows the surgeon to operate in a comfortable position without looking one direction (towards the monitor) while manipulating handles of surgical instruments that are oriented in another direction (for example, into the patient's abdomen). As more fully described in U.S. Pat. No. 5,696,837, the full disclosure of which is incorporated herein by reference, a computer processor of the servomechanism can be used to maintain the alignment between hand input devices of the controller with the image of the surgical end effectors displayed on the monitor using coordinate system transformations. This allows the surgeon to operate in a natural position using anthropomorphic hand input devices and motions aligned with the image display, despite the fact that the actual surgical instruments are inserted via otherwise awkward arbitrary access positions.

A variety of linkage arrangements have been proposed for use as a robotic surgical manipulator during minimally invasive robotic surgery. An exemplary linkage arrangement is described in U.S. Pat. No. 5,800,423, the full disclosure of which is incorporated herein by reference. In one embodiment, this linkage makes use of a parallelogram arrangement of members to hold an instrument having a shaft. Such a manipulator structure can constrain movement of the instrument having a shaft so that the instrument pivots about a center of spherical rotation positioned in space along the length of the rigid shaft. By aligning this center of rotation with the access point to the internal surgical site (for example, with the trocar or cannula at the abdominal wall during laparoscopic surgery), an end effector of the surgical instrument can be positioned safely by moving the proximal end of the shaft using the manipulator linkage without imposing dangerous forces against the abdominal wall. Alternative manipulator structures are described, for example, in U.S. Pat. Nos. 5,445,166; 5,855,583; 5,808,665; and 5,184,601; the full disclosures of which are incorporated herein by reference.

While the minimally invasive robotic surgery systems proposed to date appear to offer tremendous advantages for performing a wide variety of procedures, still further improvements would be desirable. In general, it would be desirable to provide improved structures and systems for performing robotic surgery. More specifically, it would be beneficial to enhance the efficiency and ease of use of these systems. For example, it would be beneficial to facilitate the alignment of a surgical manipulator with a desired surgical access point. It would further be desirable to allow the surgeon to begin manipulating tissues immediately upon insertion of the surgical instruments and imaging system, with little or no delay in aligning the hand input devices with the actuation servomechanisms. It would further be desirable to provide robotic surgery systems which could be moved between multiple operating rooms without requiring major structural modifications, complex alignment procedures, or unusual peripheral equipment for the operating room, hospital, or procedure site. It would be best if these improvements allowed normal operating room personnel to rapidly arrange and prepare the robotic surgery system for surgery with little or no specialized training, and with as little impact as possible on the overall cost and complexity of the system.

SUMMARY OF THE INVENTION

The present invention provides improved robotic surgery systems, structures, and methods. In general, the invention enhances the efficiency and accuracy of robotic systems by providing techniques for aligning the motion and structure of the robotically controlled manipulators and end effectors with both the internal surgical site and each other. In many embodiments, the invention makes use of manually positionable linkages supporting the surgical instruments. These linkages will often maintain a fixed configuration and/or position until a brake system is released. While the brake is held in a released mode, the fixable linkage allows the operating room personnel to manually move the linkage into alignment with the surgical site. The brake system will often fix the configuration of these passive linkages whenever the operator lets go, thereby avoiding inadvertent movement of the surgical instruments. In the exemplary embodiment, manually repositionable joints of the positioning linkage allow the operator to translate the surgical manipulator and instrument in three dimensions, and to orient the surgical instrument by rotating the manipulator and instrument about three axes of rotation. Positioning of these structures is generally facilitated by using a counter-balanced linkage system, and/or by using an inherently balanced linkage system (for example, a selective Compliance Assembly Robot Arm or "SCARA," a revolute arm in which the joint axes are vertical).

Advantageously, once the linkages supporting the surgical manipulator, instruments, and the imaging mechanism are in position, the robotic system can automatically calculate the desired coordinate system transformations so as to align hand inputs at the master controller relative to a display system with the displayed movements of the surgical instruments end effector. This capability can be provided by including a sensor system coupled to the fixable linkage. By measuring the angle of each rotational joint and the position of each sliding joint, a processor of the servomechanism can ensure that when the surgeon moves a hand input device to her right, the image of the end effector moves to the right on the controller's display. Multiple fixable positioning linkages will often extend from a common base to the driven linkages of the robotic surgical manipulators, so that the manipulator structures can be easily moved to the desired position for surgery, and so that the relative position of each manipulator can be calculated from the sensor system. This also allows positioning of the manipulators while the surgical instrument is at or near the center of travel of the manipulator, thereby decreasing the possibility that a surgical procedure will be interrupted by a limitation in the range of motion of the manipulator.

In a first aspect, the invention provides a robotic surgery system comprising a base, a surgical end effector, and robotic linkage supporting the end effector relative to the base. The linkage comprising a plurality of driven joints coupled to a servomechanism for moving the end effector so as to manipulate tissues. The linkage also includes a plurality of releasably fixable joints for pre-configuring the linkage. A joint sensor system couples the fixable joints to the servomechanism. The sensor system generates joint configuration signals.

In another aspect, the invention provides a support structure for supporting a first robotic surgical manipulator relative to a second robotic surgical manipulator. Each surgical manipulator is coupled to a servomechanism so as to robotically manipulate tissues of a patient body with a surgical end effector. The support structure comprises a base coupled to the first manipulator. The manipulator support moveably supports the second manipulator relative to the base. A sensor system couples the manipulator support to the servomechanism. The sensor system transmits manipulator position signals to the servomechanism. Servomechanism calculates a position or orientation of the first manipulator relative to the second manipulator using the signals.

In yet another aspect, the invention provides a robotic surgery system comprising a base, a surgical end effector and a manipulator supporting the end effector. The manipulator has a rigid shaft and constrains movement of the shaft to rotation about a pivot point along the shaft. An imaging system is oriented toward the end effector. The imaging system has a field of view defining a coordinate system. A linkage supports the manipulator relative to the base. A brake system restrains articulation of the linkage. The brake system is releasable to allow manual movement of the pivot point of the manipulator relative to the base. A servomechanism drivingly engages the manipulator for robotic manipulation of tissues with the end effector. A hand input controller is coupled to the servomechanism. The controller has a controller coordinate system. A sensor system is coupled to the linkage so as to generate linkage configuration signals. A processor is coupled to the sensor system and the servomechanism. The processor uses the linkage position signals to calculate a coordinate system transformation so as to coordinate controller inputs with a displayed image of the end effector.

In yet another system aspect, the invention provides a transportable robotic surgery system comprising a cart having rolling elements for moving the cart between operating rooms. A plurality of robotic arms are supported by the cart. A plurality of surgical implements are supported by the arms. A control station is couplable to the cart for directing robotic surgery.

In a first method aspect, the invention provides a method for preparing for robotic surgery. The method comprises maintaining driven joints of a robotic surgical manipulator sufficiently near mid-points of travel of the joints, so as to avoid interference with a limit of travel of the manipulator within an intended worksite. The robotic manipulator is pre-positioned by manually articulating a linkage (the linkage generally supporting the manipulator relative to a base) while maintaining the driven joints near the mid-points. The positioned manipulator is restrained with a brake system so as to prevent articulation of the linkage.

In another method aspect, the invention provides a method for performing robotic surgery. The method comprises positioning a robotic surgical manipulator by manually articulating a linkage. The positioned manipulator is restrained with a brake system so as to prevent manual articulation of the linkage. A surgical end effector, which is supported by the positioned manipulator, is imaged in an imaging coordinate system. The restrained manipulator is actuated with a servomechanism by actuating a controller in a controller coordinate system so as to robotically manipulate tissue with the end effector. The controller coordinate system is transformed to the imaging coordinate system by sensing joint configurations of the restrained linkage. The imaged end effector is displayed so that controller inputs correlate with end effector movements.

In yet another method aspect, the invention provides a method for performing robotic surgery. The method comprises manually moving a manipulator relative to a base by articulating a plurality of fixable joints. A brake is actuated to inhibit inadvertent manual movement of the positioned end effector from articulation of the fixable joints. Tissue is manipulated with the end effector by actuating a plurality of driven joints of the linkage with a servomechanism. Positions of the fixable joints are sensed and transmitted to the servomechanism.

BRIEF DESCRIPTION OF THE DRAWINGS

FIG. 5 is a perspective view of a positioning linkage which allows the robotic manipulators to be pre-positioned manually, and also illustrates the potentiometers used to sense the joint angles.

DESCRIPTION OF THE SPECIFIC EMBODIMENTS

Figure 1:
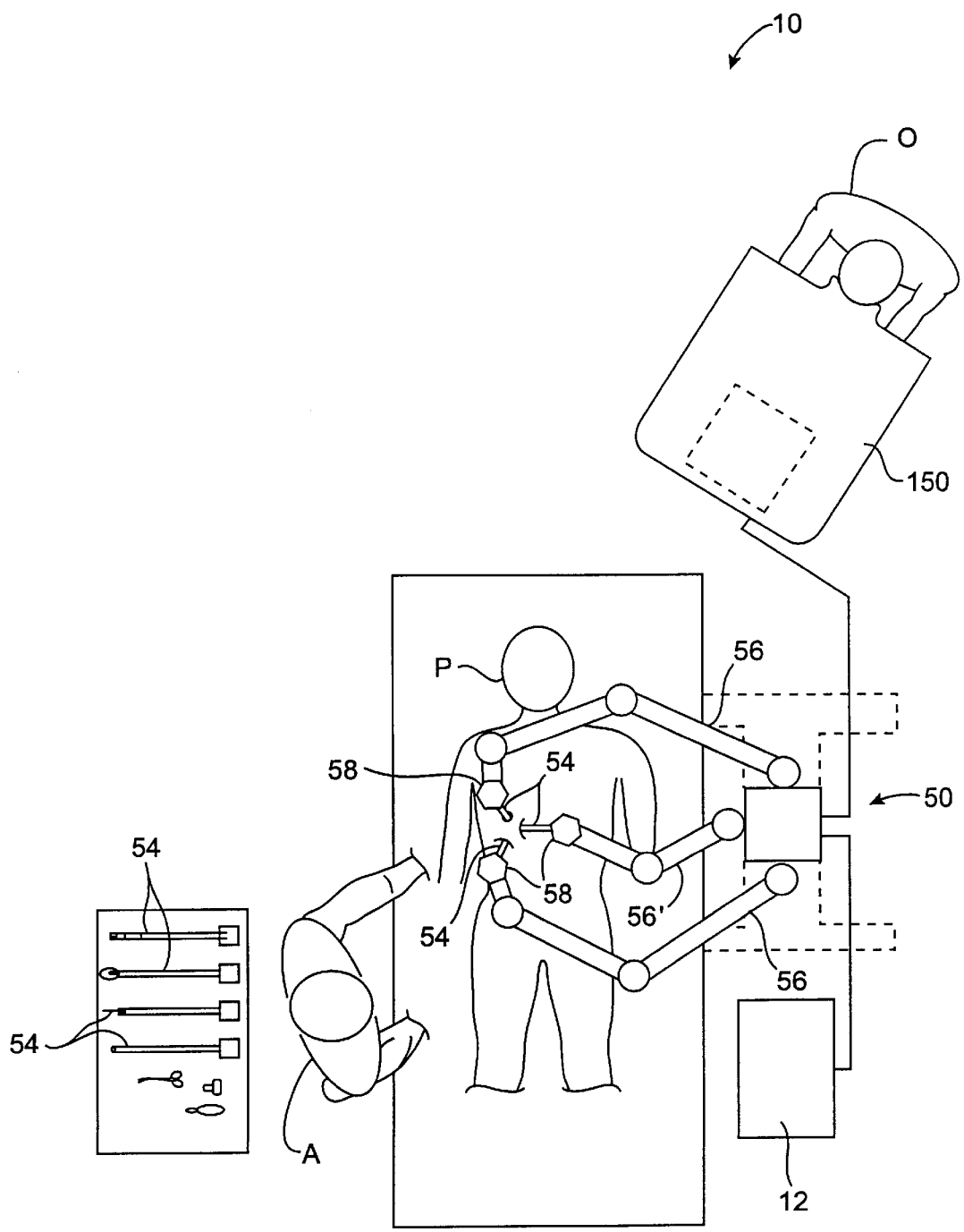
FIG. 1 is a plane view showing a robotic surgical system performing a minimally invasive robotic surgical procedure.

The present invention provides robotic surgery systems, devices, and methods. Robotic surgery will generally involve the use of multiple robotic manipulator arms. One or more of the robotic manipulator arms will often support a surgical tool which may be articulated (such as jaws, scissors, graspers, needle holders, micro dissectors, staple appliers, tackers, suction/irrigation tools, clip appliers, or the like) or non-articulated (such as cutting blades, cautery probes, irrigators, catheters, suction orifices, or the like). One or more of the arms will often be used to support a surgical image capture device such as an endoscope (which may be any of a variety of structures such as a laparoscope, an arthroscope, a hysteroscope, or the like), or, optionally, some other imaging modality (such as ultrasound, fluoroscopy, magnetic resonance imaging, or the like). Typically, the arms will support at least two surgical tools corresponding to the two hands of a surgeon and one image capture device.

Mounting the robotic manipulator arms to a single cart structure allows the robotic surgery system of the present invention to be moved efficiently from operating room to operating room. This can avoid construction of specialized robotic operating rooms, and can allow a hospital to take advantage of the flexibility of robotic surgery to perform a variety of surgical procedures, including open surgery, neurosurgical procedures (such as stereotaxy), endoscopic procedures (such as laparoscopy, arthroscopy, thoracoscopy), and the like.

Mounting of multiple robotic manipulator arms with the arms supported by one or more positioning linkages attached to a common base also allows the computer system that controls robotic movements to determine the position of the end effectors and robotic arms relative to each other. This can be used for a variety of purposes, including transforming an image capture coordinate system to a hand input controller coordinate system so as to align the surgeon's inputs with movements of the end effectors as displayed to the surgeon. In some embodiments, the computer may also calculate the positions of the robotic manipulators to avoid interference as the implements are manipulated during surgery. For example, solid modeling of the robotic manipulator structure may be used to prevent two arms from striking each other, thereby avoiding damage to the robotic structure and potential injury to the patient. This common base may also maximize access to the patient before, during, and after the robotic surgical procedure, as the cart will typically be situated along one side of the operating table, leaving the other side available for access by surgeons and surgical assistants.

In light of these capabilities, the present invention will find applications in a variety of surgical procedures. The most immediate applications will be to improve existing minimally invasive surgical procedures, such as coronary artery bypass grafting and mitral and aortic valve repair and/or replacement. The invention will also have applications for surgical procedures which are difficult to perform using existing minimally invasive techniques, such as Nissen Fundoplications. Additionally, it is anticipated that these surgical systems will find uses in entirely new surgeries that would be difficult and/or impossible to perform using traditional open or known minimally invasive techniques. In the meantime, additional potential applications include vascular surgery (such as for the repair of thoracic and abdominal aneurysms), general and digestive surgeries (such as cholecystectomy, inguinale hernia repair, colon resection, and the like), gynecology (for fertility procedures, hysterectomies, bladder neck suspensions, and the like), and a wide variety of alternative procedures.

The positioning linkage devices, systems, and methods described hereinbelow will generally be used within a robotic surgery system such as the described in co-pending U.S. patent application Ser. No. 08/975,617, filed Nov. 21, 1997, the full disclosure of which is incorporated herein by reference.

Referring now to FIG. 1, an operator O (generally a surgeon) performs a minimally invasive surgical procedure on patient P by manipulating input devices at a surgeon's console 150. A computer of console 150 directs movement of endoscopic surgical instruments 54, effecting movement of the instruments using a robotic patient-side cart system 50. An assistant A assists in pre-positioning of the manipulator relative to patient P in swapping tools or instruments 54 for alternative tool structures, and the like, while viewing the internal surgical site via an assistant display 12. The image of the internal surgical site shown to assistant A and operator O by the assistant display and surgeon's console is provided by one of the surgical instruments supported by cart 50.

Typically, cart 50 includes at least three robotic manipulator arms supported by linkages, with the central arm supporting an endoscope and the outer arms supporting tissue manipulation tools.

Generally, the arms of cart 50 will include a positioning portion which remains in a fixed configuration while manipulating tissue, and a driven portion which is actively articulated under the direction of surgeon's console 150. The actively driven portion is herein referred to as a manipulator 58. The fixable portion of the cart linkage structures may be referred to as a positioning linkage and/or a "set-up joint" 56, 56'.

Figure 2:
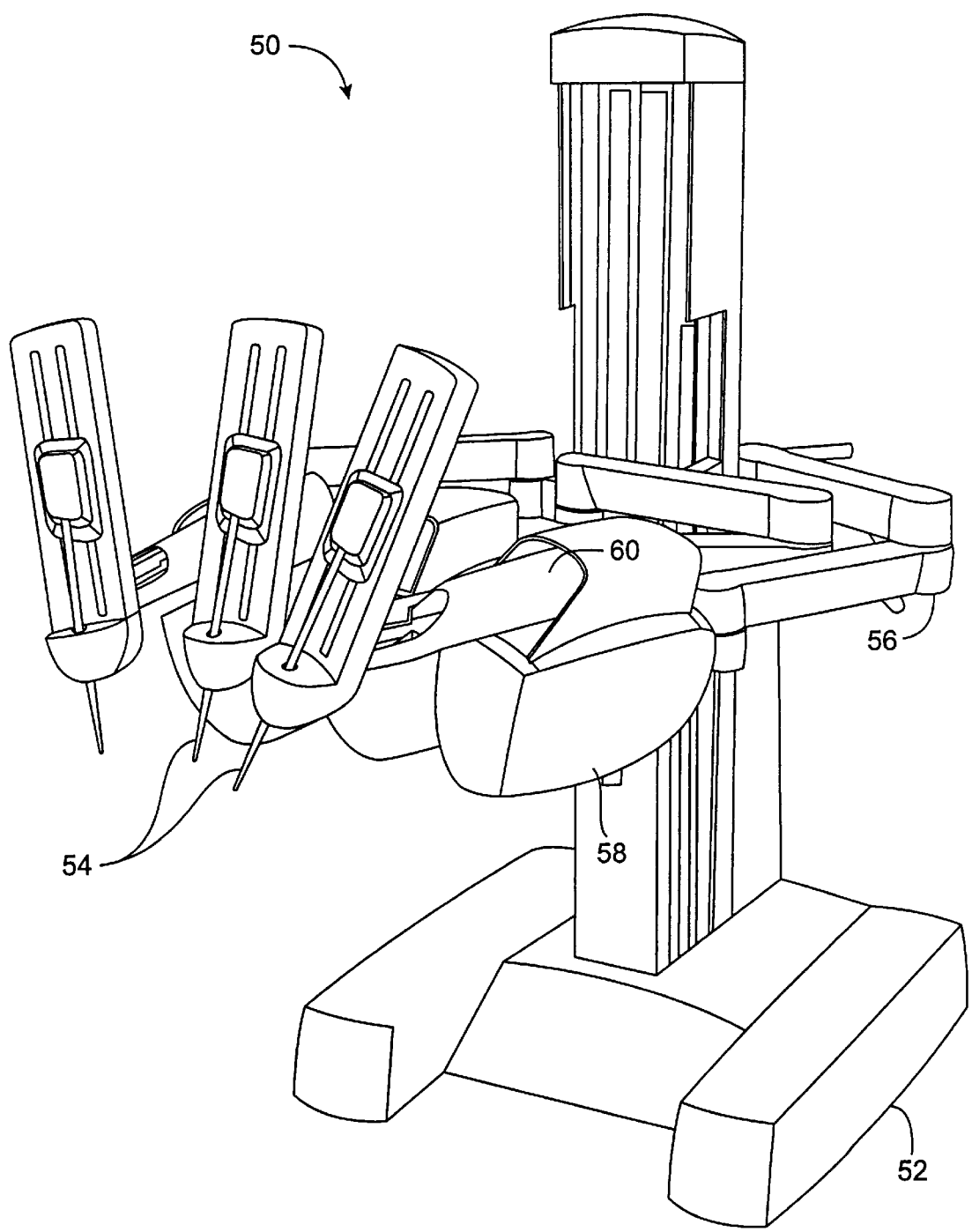
FIG. 2 is a perspective view of a robotic surgical patient-side cart system in which positioning linkages having a series of manually articulatable, fixable joints support three robotically actuated manipulators.
Figure 2A:
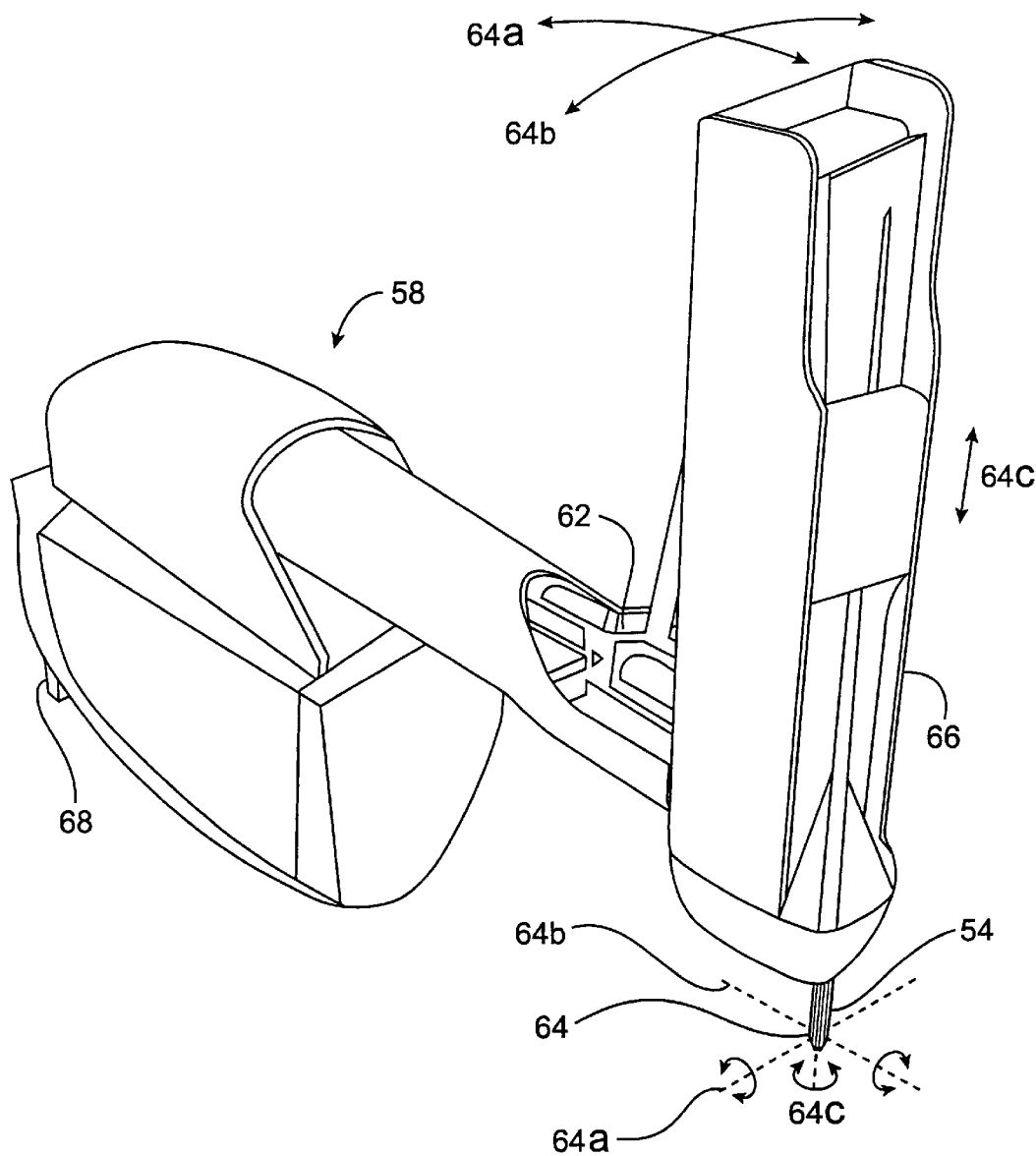
FIG. 2A is a perspective view of a robotic surgical manipulator for use in the cart system of FIG. 2.

Robotic arm cart 50 is shown in isolation in FIG. 2. Cart 50 includes a base 52 from which three surgical implements 54 are supported. More specifically, implements 54 are each supported by a positioning linkage 56 and a robotic manipulators 58. It should be noted that these linkage structures are here illustrated with protective covers extending over much of the robotic linkage. It should be understood that these protective covers are optional, and may be limited in size or entirely eliminated in some embodiments to minimize the inertia that is manipulated by the servomechanism, and to limit the overall weight of cart 50.

Cart 50 will generally have dimensions suitable for transporting the cart between operating rooms. The cart will typically fit through standard operating room doors and onto standard hospital elevators. The cart should have a weight and wheel (or other transportation) system that allows the cart to be positioned adjacent an operating table by a single attendant. The cart should have sufficient stability in the transport configuration to avoid tipping at minor discontinuities of the floor, and to easily withstand overturning moments that will be imposed at the ends of the robotic arms during use.

Referring now to FIGS. 2 and 2A–C, robotic manipulators 58 preferably include a linkage 62 that constrains movement of tool 54. More specifically, linkage 62 includes rigid links coupled together by rotational joints in a parallelogram arrangement so that tool 54 rotates around a point in space 64, as more fully described in issued U.S. Pat. No. 5,817,084, the full disclosure of which is incorporated herein by reference. The parallelogram arrangement constrains rotation to pivoting about an axis 64a, sometimes called the pitch axis. The links supporting the parallelogram linkage are pivotally mounted to set-up joints 56 (see FIG. 2) so that tool 54 further rotates about an axis 64b, sometimes called the yaw axis. The pitch and yaw axes intersect at the remote center 64, which is aligned along a shaft 66 of tool 54.

Tool 54 has still further driven degrees of freedom as supported by manipulator 58, including sliding motion of the tool along insertion axis 64c (the axis of shaft 66), sometimes referred to as insertion. As tool 54 slides along axis 64c relative to manipulator 58, remote center 64 remains fixed relative to base 68 of manipulator 58. Hence, the entire manipulator is generally moved to re-position remote center 64.

Figure 2B:
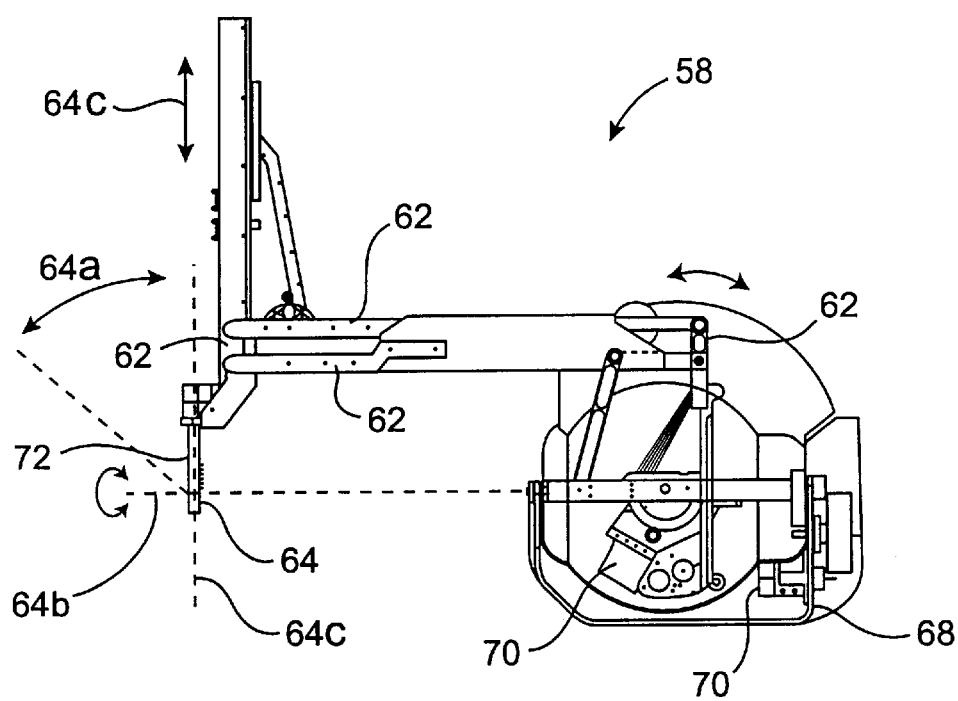
FIGS. 2B and C are side and front views, respectively, of the linkage of the robotic manipulator of FIG. 2, showing how the manipulator maintains a remote center of rotation along a shaft of a surgical instrument.
Figure 2C:
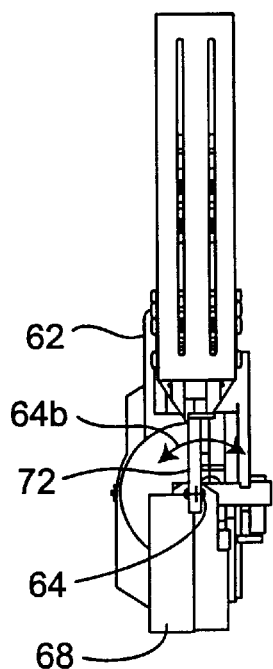

Linkage 62 of manipulator 58 is driven by a series of motors 70 (see FIG. 2B). These motors actively move linkage 62 in response to commands from a processor. Motors 70 are further coupled to tool 54 (see FIG. 2) so as to rotate the tool about axis 64c, and often to articulate a wrist at the distal end of the tool about at least one, and often two, degrees of freedom. Additionally, motors 70 can be used to actuate an articulatable end effector of the tool for grasping tissues in the jaws of a forceps or the like. Motors 70 may be coupled to at least some of the joints of tool 54 using cables, as more fully described in U.S. Pat. No. 5,792,135, the full disclosure of which is also incorporated herein by reference. As described in that reference, the manipulator will often include flexible members for transferring motion from the drive components to the surgical tool. For endoscopic procedures, manipulator 58 will often include a cannula 72. Cannula 72, which may be releasably coupled to manipulator 58, supports tool 54, preferably allowing the tool to rotate and move axially through the central bore of the cannula.

Figure 3:
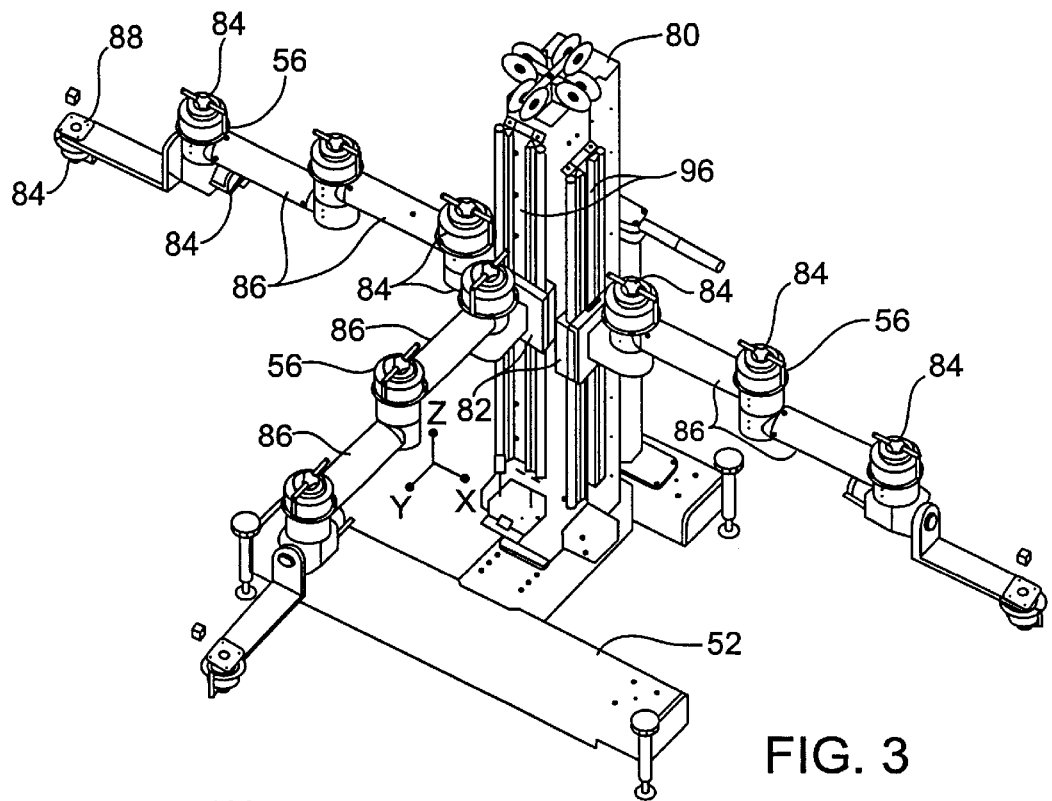
FIG. 3 is a perspective view of the patient-side cart structure and positioning linkages which support the robotic manipulators in the system of FIG. 2.

As described above regarding FIG. 2, manipulator 58 is generally supported by a positioning linkage 56. Exemplary positioning linkage structures are illustrated in FIG. 3. The exemplary positioning linkage system includes three types of structures. First, a vertical column 80 supports vertically sliding joints 82 that are used to position manipulator 58 (see FIG. 2) along the vertical or Z axis. Second, rotary joints 84 separated by rigid links 86 are used to horizontally position manipulators 58 in the X-Y plane. Third, another series of rotary joints 84 mounted adjacent a manipulator interface 88 rotationally orients the manipulators.

Figure 4A:
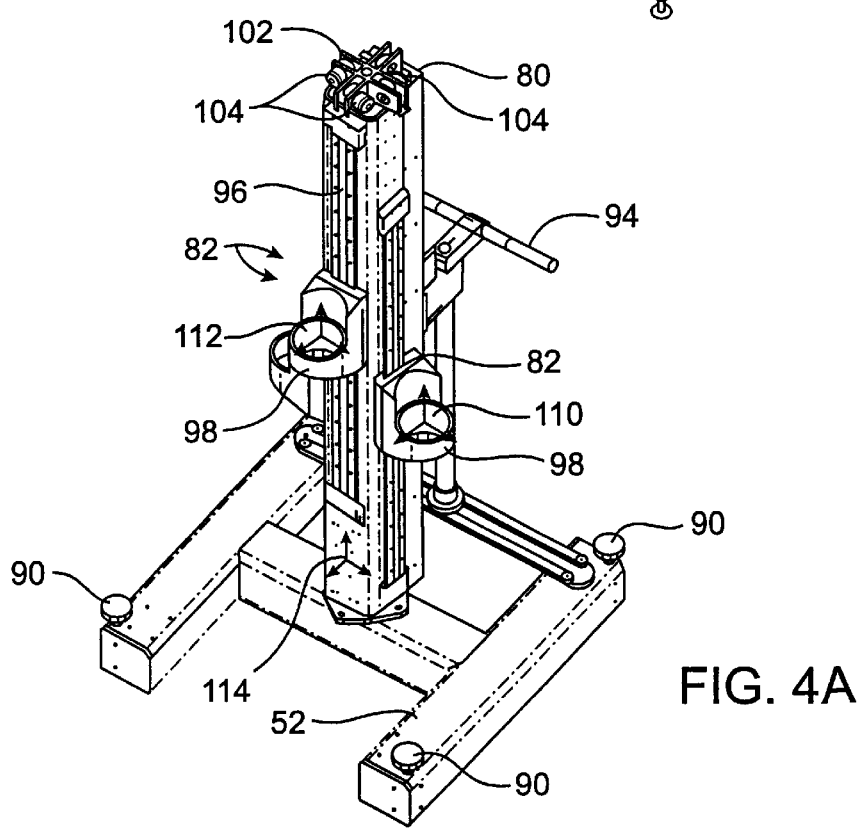
FIGS. 4A and B are front and rear perspective views, respectively, of the patient-side cart structure, showing the counter weighted vertical sliding joints which vertically position the manipulators, and also showing the steering system for the cart.
Figure 4B:
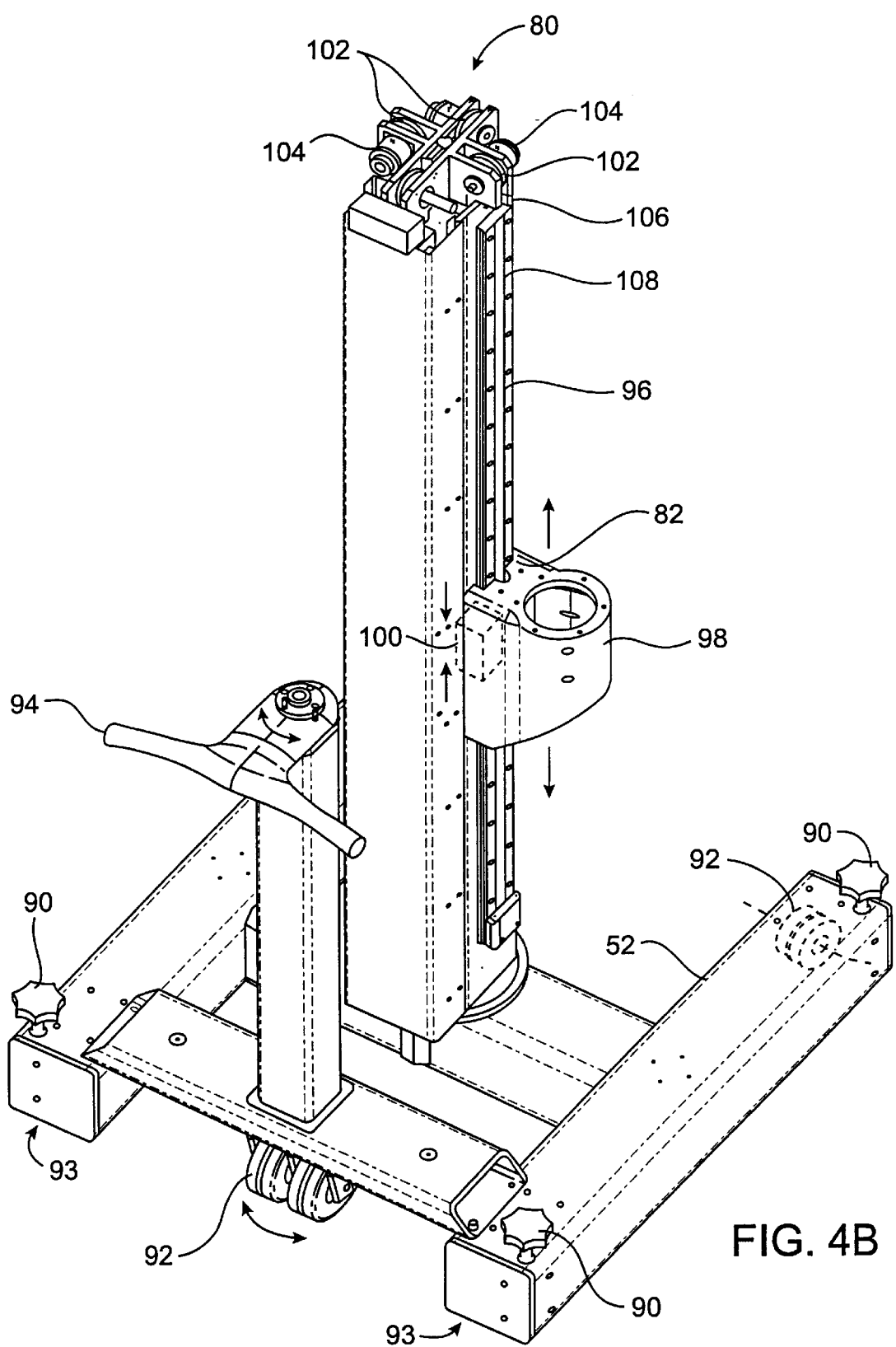

The structure of column 80, vertical sliding joints 82, and base 52 can be understood with reference to FIGS. 4A and B. Beginning with base 52, the base will generally distribute the weight of the robotic structures and the forces imposed on the entire slave system. When used for surgery, base 52 will be fixedly supported by a series of jacks 90 to avoid inadvertent movement of the robotic arms. Jacks 90 will typically be threadably coupled to the remainder of base 52, so that the jacks can be retracted for transport. When jacks 90 are retracted by rotating their handles, base 52 rests on wheels 92.

To prevent the cart from tipping as it is rolled on wheels 92, the wheels located near the front of the cart will preferably be non-swiveling. In other words, the wheels will rotate about a fixed axis relative to the base. Wheels 92 adjacent a rear portion of the cart will preferably be coupled to steering handle 94 so that the wheels and handle rotate about a steering axis. This facilitates maneuvering of the cart and positioning of the cart adjacent the operating table. Passively swiveling "outrigger" wheels 93 may be disposed outboard of the steerable wheels 92 to provide additional support if the cart begins to tip.

As the weight of base 52 generally enhances the tipping stability of the slave cart structure, and as a box section enhances stiffness, the exemplary base comprises box steel tubing, which may be welded or bolted together.

Column 80 extends upward from base 52, and may optionally also comprise a box steel structure. Sliding joints 82, including vertical tracks 96 on which sliders 98 ride, are counterbalanced by weights 100 mounted within column 80. More specifically, a cable extends upward from slider 98 and over a pulley 102, and then down from the pulley to weight 100 within column 80. Weight 100 preferably has a mass that is substantially equal to the combined mass of the slider 98, positioning linkage 56, manipulator 58, and tool 54. This allows the robotic arms to be re-positioned upward or downward with very little effort. It should be understood that weight 100 is schematically illustrated, and may have an actual length of about 24 in. or more.

To prevent inadvertent movement of sliding joint 82, pulleys 102 are coupled to column 80 by brakes 104. These brakes prevent rotation of the pulleys when slider 98 is positioned, as will be described in more detail hereinbelow.

As described above, it is often advantageous to identify the configuration of the manually movable, as well as the active, joints so as to allow the processor of the robotic system to perform coordinate transformations, calculate relative positions of surgical end effectors, and the like. Toward that end, sliding joints 82 include sensors 106 coupled to sliders 98 or counterweights 100 by cables 108. Sensors 106 comprise accurate potentiometers that generate electrical signals which vary with the position of sliders 98 along tracks 96. As the structure and position of sliding joints 82 relative to column 80 is known, knowing the axial position of sliders 98 allows the processor to perform transformations between first and second slider coordinate systems 110, 112 and a reference base coordinate system 114. Similarly, by knowing the angles defined by each rotary joint 84, transformations between the slider joints and a manipulator base can also be calculated. It should be understood that these interim coordinate system transformations need not be performed, but that they are representative of the total transformation to be performed. Regardless, where the configuration of all joints between base 52 and the end effectors of tools 54 are known, the processor can accurately determine the position and orientation of the end effector, as well as how to effect movement in a desired direction by articulating one or more of the driven joints.

Each sensor preferably may comprise redundant potentiometers that "self-check" one another. That is, information from the redundant potentiometers may be compared with a selected tolerance to ensure to a degree of accuracy that the positioning of the corresponding joint is correctly known. If the information from the redundant potentiometers fail to match, the operator may be informed of this fact and/or the set-up may be interrupted or delayed until corrective action is taken. Additionally, the operator may be able to override such an interrupt if desired. Potentiometers on the set-up linkage may be also checked for movement, to warn an operator of unintended movement of the normally locked and stationary set-up linkages during an operation, such as might be due to an assistant unintentionally leaning against the linkage.

The structure of positioning linkage 56 is illustrated in more detail in FIG. 5. Positioning linkage 56 is supported by slider 98, and include first and second elongate links 120, 122. First link 120 is coupled to slider 98 by rotational joint 84a, and is coupled to second link 122 by rotational joint 84b. As described above, slider 98 moves up and downward (along the z-axis) to vertically position the manipulator and remote center of rotation. Pivoting of the first and second linkages relative to the slider and to each other allows the manipulator to move horizontally (in the X-Y plane). As rotational joints 84a and 84b rotate about vertical axes, the height of the manipulator does not change when these joints rotate and no counterbalancing is required.

Rotational joints 84 generally include a brake 124 and a sensor 126. Brake 124 prevents rotation about the joint unless the brake is released. In other words, the brake is normally on (so that the joint is in a fixed configuration). This prevents inadvertent articulation of positioning linkage 56 during a surgical procedure, and also avoids movement if power to the robotic system is lost. The brakes may be safely overcome (so as to articulate the joints without damage) with a reasonable amount of manual force against the linkage or manipulator, thereby providing a safety feature if power is lost.

A wide variety of alternative brake structures could be used in place of the exemplary embodiment described above. Suitable brakes may be actuated electrically, pneumatically, hydraulically, or the like, and may be located at the joint axis (as shown) or may coupled to the joint using gears, cables, rigid linkages, or the like.

Sensors 126 of joints 84 generate electrical signals which indicate the rotational angle defined by the joint. Sensors 126 preferably generate absolute angle indication signals that vary with the absolute angle defined by the joint, rather than generating a signal which indicates a change in the angle. This avoids having to regularly return the joints to a zero position to provide an accurate angle measurement. Although absolute angle measurement devices are generally preferred, in some embodiments sensors 126 may comprise encoders that measure a number of discrete changes in the joint angle, or a wide variety of alternative structures.

Links 120 and 122 may be formed of a wide variety of high strength, light weight materials. Alternative structures might include aluminum or composites, such as graphite or the like. In general, minimizing the weight of the set-up joints and manipulator structures can dramatically decrease the total weight of the robotic cart, as the structures are often counterbalanced and any added weight generally increases the cart base weight to avoid tipping.

Positioning of the manipulator in preparation for surgery is facilitated by providing a handle 128 affixed to the distal end of second link 122. Handle 128 has an actuation button 130 that releases brakes 124 so as to allow movement of set-up joints 56. As described above, the joints will preferably remain locked unless a signal is provided by circuitry coupled to actuation button 130. Affixing handle 128 on or near the manipulator support interface allows the positioning linkage to be moved without imposing undue forces against the servomechanism of the manipulator structure.

In addition to the positional capabilities of positioning linkage 56, rotational joints 84c, d, and e allow the manipulator structure to be rotated to a desired orientation. Including the vertical adjustability provided by sliding joint 82, positioning linkage 56 allows the manipulator to be positioned with six degrees of freedom relative to base 52 of the robotic arm cart. As illustrated, one or more orientational degrees of freedom may be provided between the handle and the manipulator. As each of the rotational joints 84 and the sliding joint 82 include a sensor coupled to a processor of the servomechanism, the servomechanism can calculate a position and orientation of a manipulator interface 132 on which the manipulator is mounted, and can also perform the coordinate system transformations described hereinabove.

In the exemplary embodiment, the brakes 124 at all of the joints on one of the three positioning linkage 56 supporting a manipulator 58 are actuated in unison by actuation button 130 on handle 128, allowing the operating room personnel to position and orient the manipulator freely. The manipulator structure will preferably be balanced about rotational joints 84d and 84e, as these joints may rotate about axes that are at an angle from vertical. Fabricating the manipulator or adding counterbalance weights to the manipulator so that the center of mass of the manipulator is aligned along the axes of rotation of these two joints (as illustrated in FIG. 3) will prevent the operating room personnel from having to overcome a righting moment when rotationally positioning the manipulator.

Figure 6:
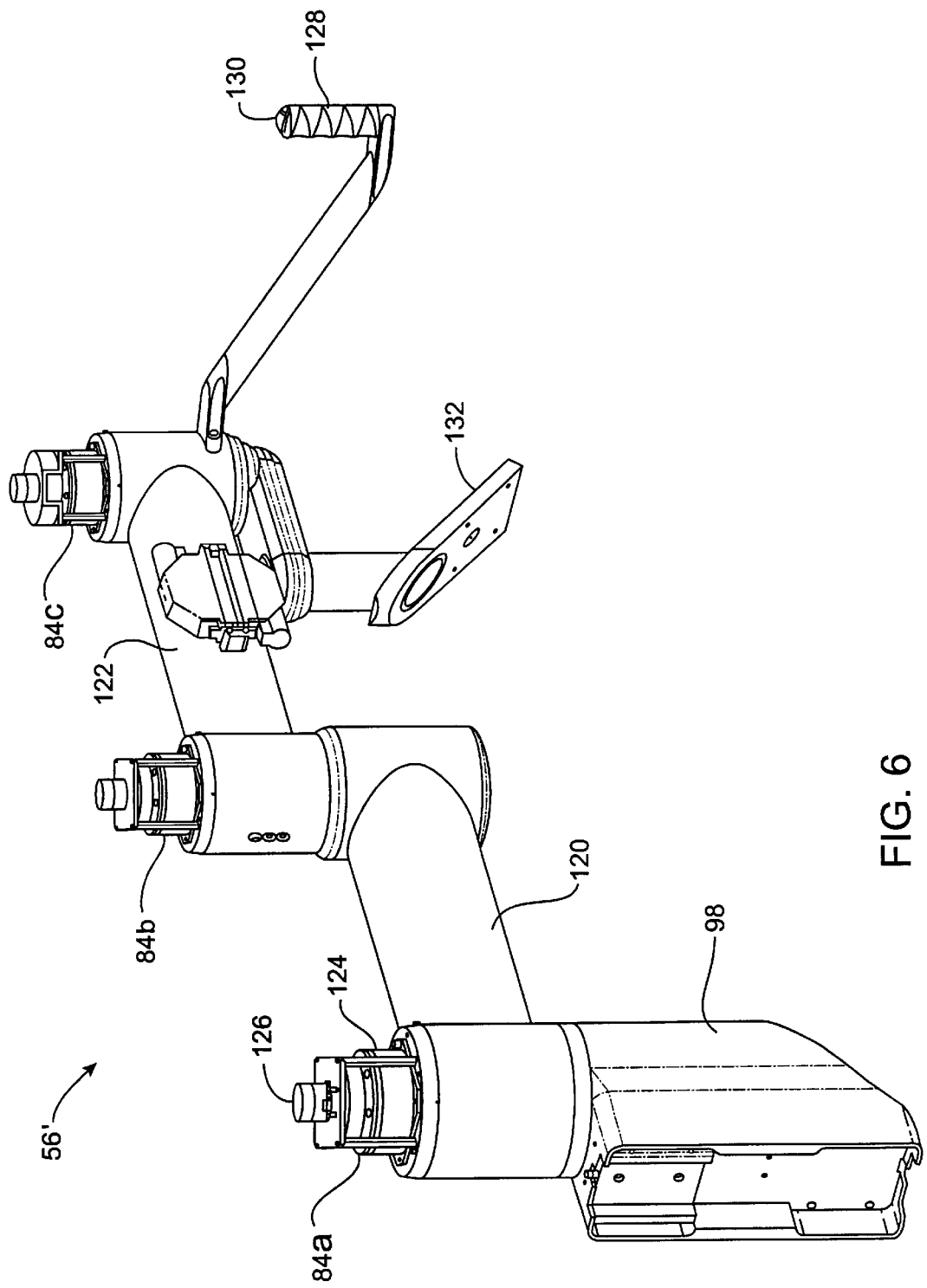
FIG. 6 is a perspective view of a positioning linkage used for manual positioning of a laparoscope in preparation for surgery, and also illustrates the potentiometers used to sense the joint angles.

Referring now to FIG. 6, it may not be necessary to provide a fill six degrees of freedom for each set of the set-up joints. For example, positioning linkage 56' provide each of the positional degrees of freedom described above, but with more limited orientational adjustment capabilities. When, for example, an endoscope is supported by a manipulator having four degrees of freedom (such as pitch, yaw, insertion, and roll about the scope's axis) the manipulator need not be supported by a positioning linkage with six degrees of freedom for many surgical procedures. Manipulator interface 132 is here coupled to the distal end of second link 122 by a single rotational joint 84c. As the manipulator structure will have multiple degrees of freedom for the surgical implement supported thereon, this provides sufficient endoscope positioning and orienting flexibility with reduced complexity.

Figure 7:
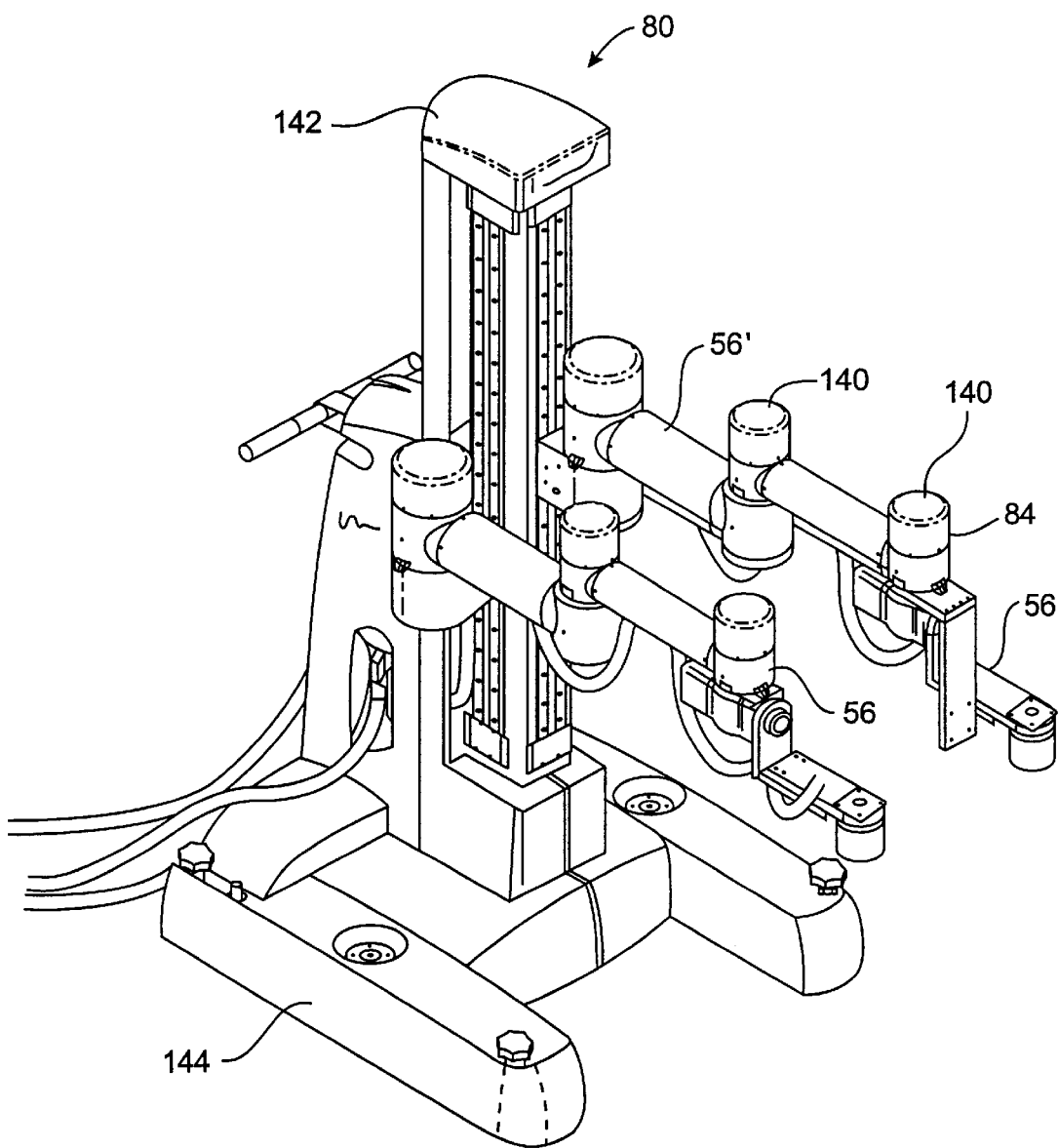
FIG. 7 is a perspective view of the patient-side cart and positioning linkages with lightweight covers protecting sensitive portions of the system.

Referring now to FIG. 7, in the exemplary robotic cart, two six degree of freedom positioning linkages 56 are supported by column 80 on either side of a four degree of freedom positioning linkages 56'. This central set-up joint is particularly well adapted for use in supporting an image capture device such as a laparoscope, endoscope, or the like. Six degree of freedom positioning linkages 56 may be used to pre-position manipulators supporting surgical implements used for manipulating tissue. This arrangement is well adapted for use by a surgeon controlling a surgical tool with each hand while viewing the procedure through the endoscope. When re-positioning of the endoscope is desired, a manipulator structure coupling the endoscope to positioning linkage 56' may be actuated with a servomechanism so as to pivot the endoscope about the insertion point, as described above.

FIG. 7 also illustrates a series of protective covers 140 mounted over the brakes and sensors of joints 84. Additionally, a column cover 142 protects the pulleys and their associated brakes. These covers help avoid injury to attending operating room personnel by limiting the number of pinch points, and also provide a more finished appearance. Similar appearance benefits are provided by mounting base and column covers 144 on their associated cart structures.

Figure 8B:
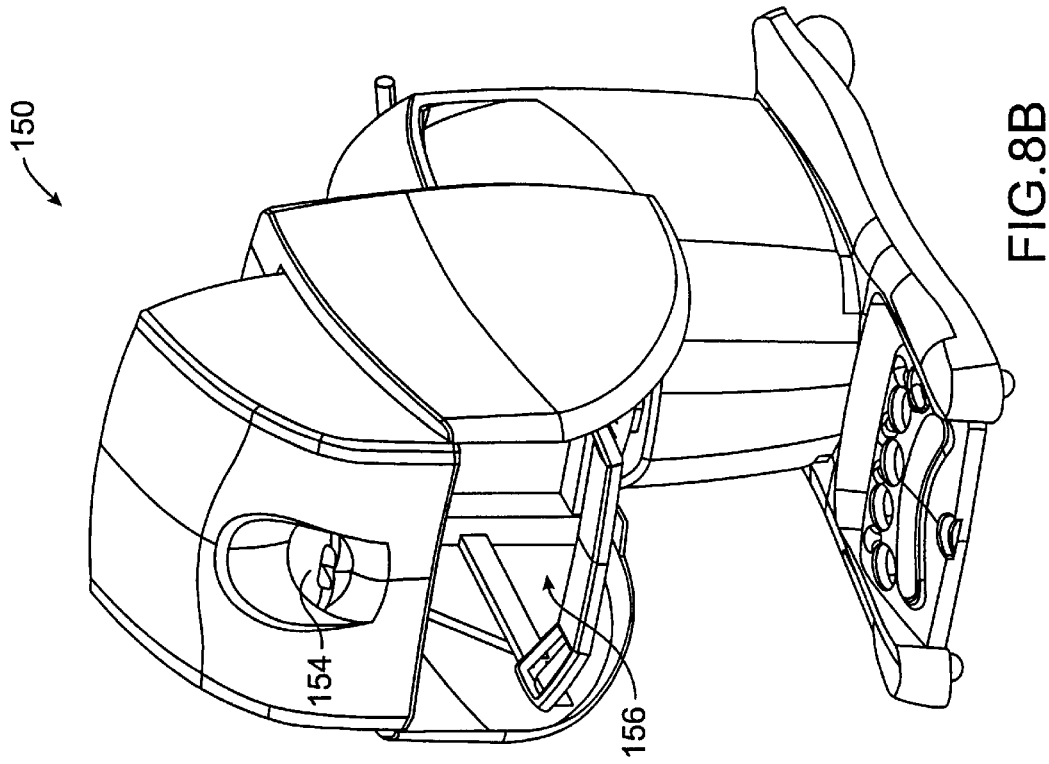
FIGS. 8A and B are rear and front views, respectively, of the surgeon's console for use in the surgical system of FIG. 1.
Figure 8A:
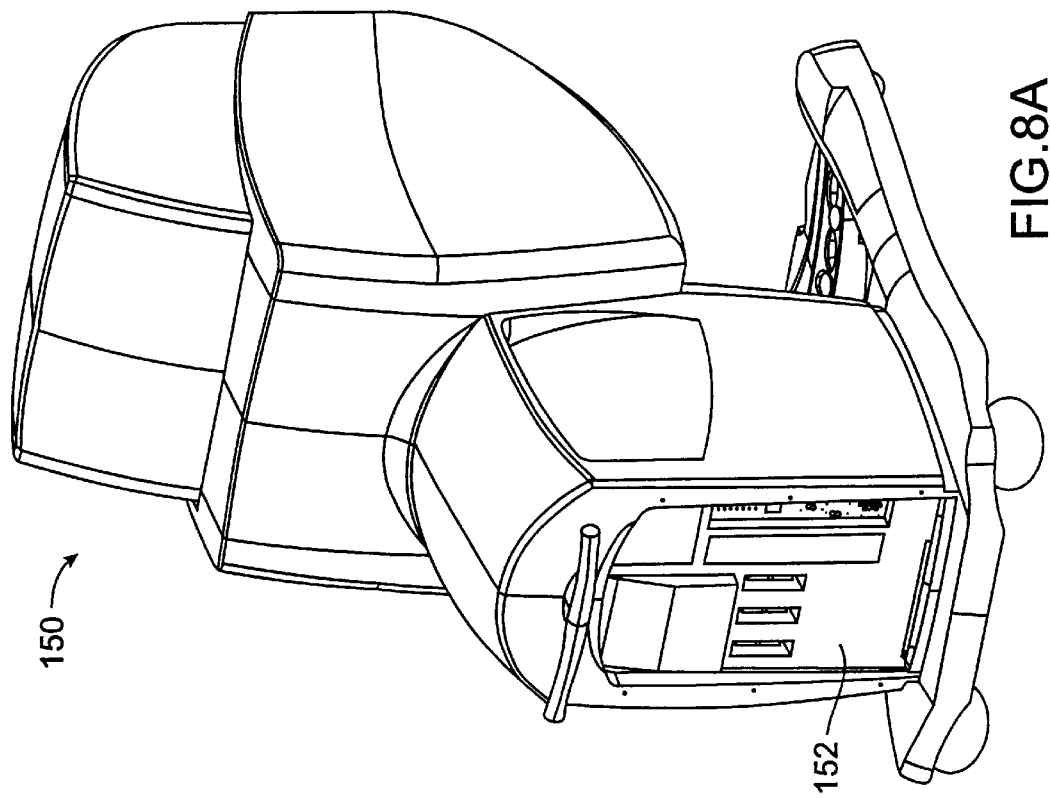
Figure 9B:
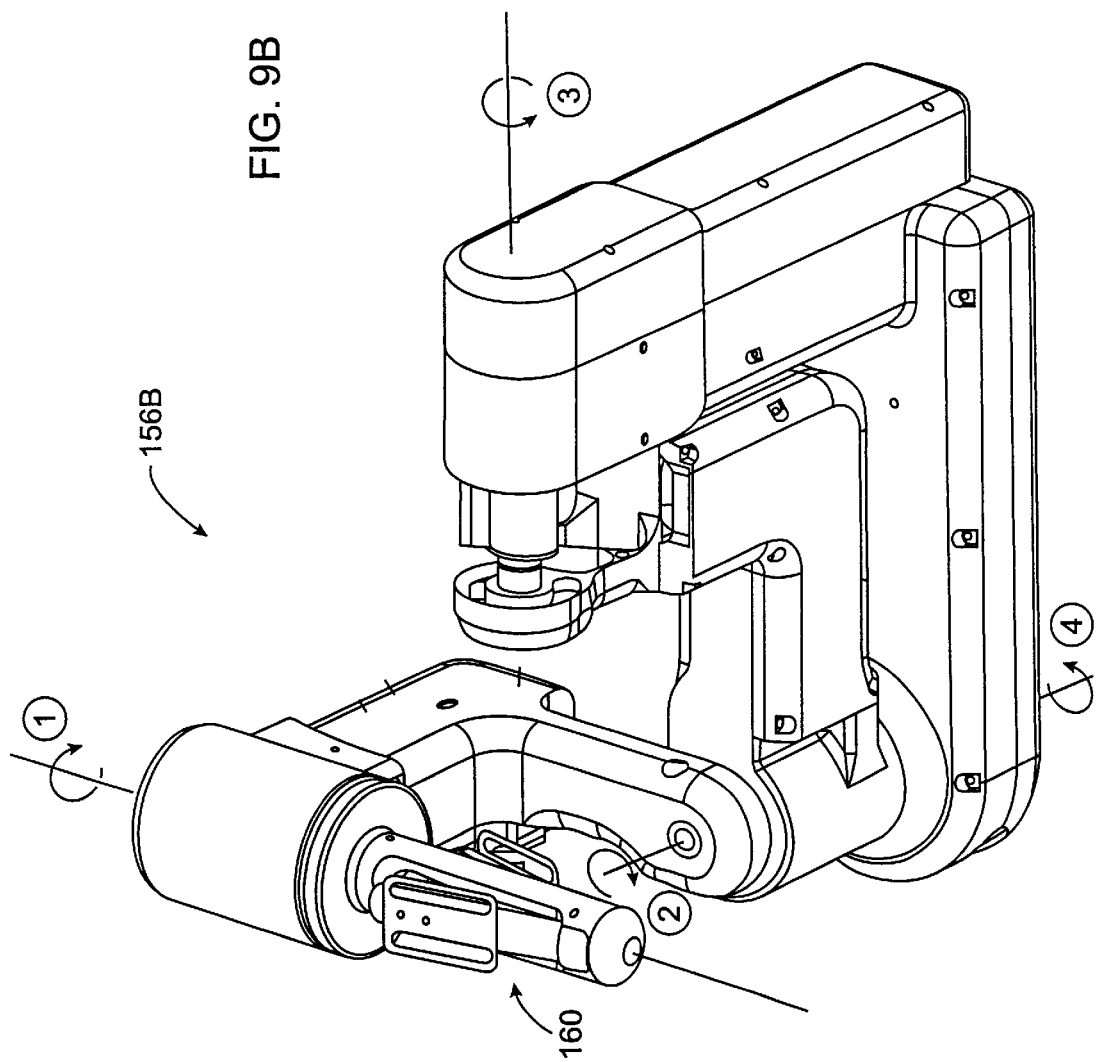
FIGS. 9A and B illustrate a master input device for use in the surgeon's console of the FIGS. 8A and B.

An exemplary surgeon's workstation is illustrated in FIGS. 8A and B. Control station 150 includes processors 152 for the robotic servomechanism. Also included in controller station 150 are a stereo imaging system 154 and a pair of controllers 156 (shown in FIGS. 9A and 9B), which hang below the imaging system.

The surgeon will generally manipulate tissues using the robotic system by moving the controllers within a three dimensional controller workspace of controller station 150. In the exemplary embodiment, the surgeon will manipulate these controllers while viewing the surgical site through display 154. Processor 152 can calculate an image capture coordinate system via the sensors in positioning linkage 56' and manipulator 58 supporting the laparoscope, and can perform coordinate system transformations so as to generate signals to the manipulator structure that maintain alignment between the three dimensional image of the end effector as viewed through display 154 and the hand controller within the controller workspace. By maintaining this alignment as the physician moves the hand controller in both position and orientation, the robotic surgery system allows the surgeon to manipulate the surgical tools as if the handle in the surgeon's hand and the end effector in the surgeon's field of view define a single contiguous surgical instrument. This provides an enhanced sense of presence and allows the surgeon to operate efficiently and accurately without performing mental coordinate transformations. The correlation between movement of the input device and image of the end effector is more fully described in U.S. Pat. No. 5,808,665 while an exemplary method and structure for performing the coordinate system transformation calculations is detailed in Provisional U.S. Patent Application Ser. No. 60/128,160 filed on Apr. 7, 1999 for a "Camera Referenced Control in a Minimally Invasive Surgical Apparatus", the full disclosures of which are incorporated herein by reference.

An exemplary master control input device or controller 156 is seen in FIGS. 9A and B. Generally, controller 156 includes an articulate arm portion 156A and a wrist or gimbal portion 156B. Articulate arm 156A primarily accommodates and senses positional or translational movement in the controller workspace, while gimbal 156B accommodates and senses an orientation of a handle 160. Articulate arm 156A includes joints which accommodate pivotal rotation about axis A, B, and C, while gimbal 156B includes rotational joints which accommodate and sense movement about orientational axis 1, 2, and 3. Gimbal 156B also moves relative to articulate arm 156A about a fourth orientational axis 4 when mounted to the arm, thereby providing a redundant orientational degree of freedom for the master input control handle. This exemplary input device is more fully described in co-pending Provisional U.S. Patent Application Ser. No. 60/111,710 filed on Dec. 8, 1998 for a "Master Having Redundant Degrees of Freedom", the full disclosure of which is incorporated herein by reference.

Figure 10:
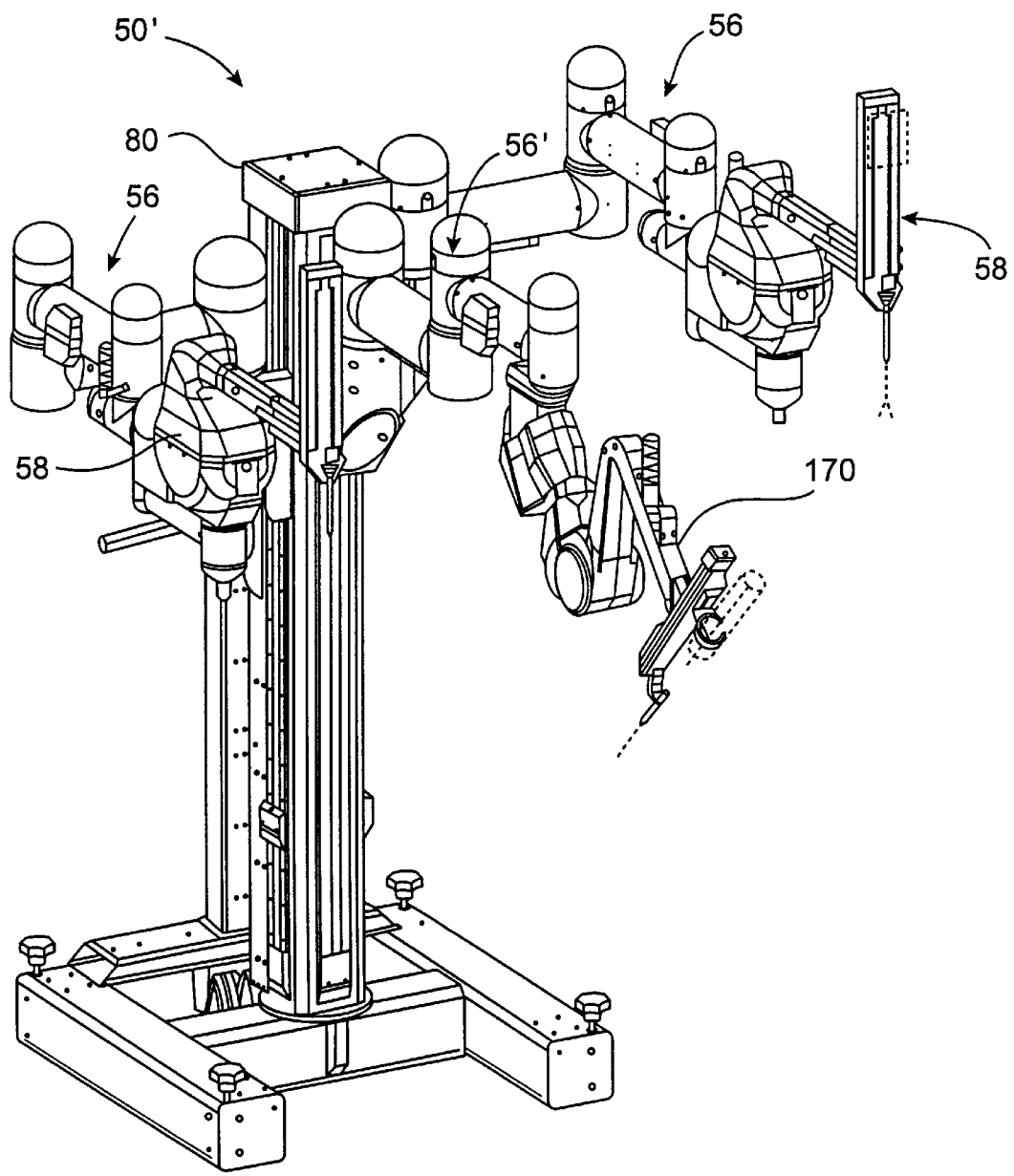
FIG. 10 is a perspective view of an alternative patient-side cart having a modified middle arm for positioning an endoscope.

Referring now to FIG. 10, an alternative cart 50', including a positioning linkage 56' with less than six degrees of freedom, supported between two six degrees of freedom positioning linkages 56. Six degree of freedom linkages 56 generally extend radially outwardly from column 80 and will often be arranged to support the surgical tools 54 (including the tissue manipulating tools and the endoscope), so that the elongated shafts of these endoscopic instruments extend radially outwardly from a pattern of apertures into an internal surgical sites, as illustrated in FIG. 1. This gives the cart system 50' an "elbows out" appearance in use, which helps enhance the clearance between the manipulators so as to avoid collisions as the manipulators move in the space over patient P during a surgical procedure. An endoscope manipulator 170 and its associated linkage 56' will often be arranged so as to extend substantially from column 80 to the endoscope, as also illustrated in FIG. 1. Endoscope manipulator 170 may not include all of the tool actuation drive system provided for articulated surgical instruments, which are typically included in manipulators 58. An exemplary endoscope manipulator is more fully described in Provisional U.S. Patent Application Ser. No. 60/112,990 filed on Dec. 16, 1998, the full disclosure of which is incorporated herein by reference.

Figure 11:
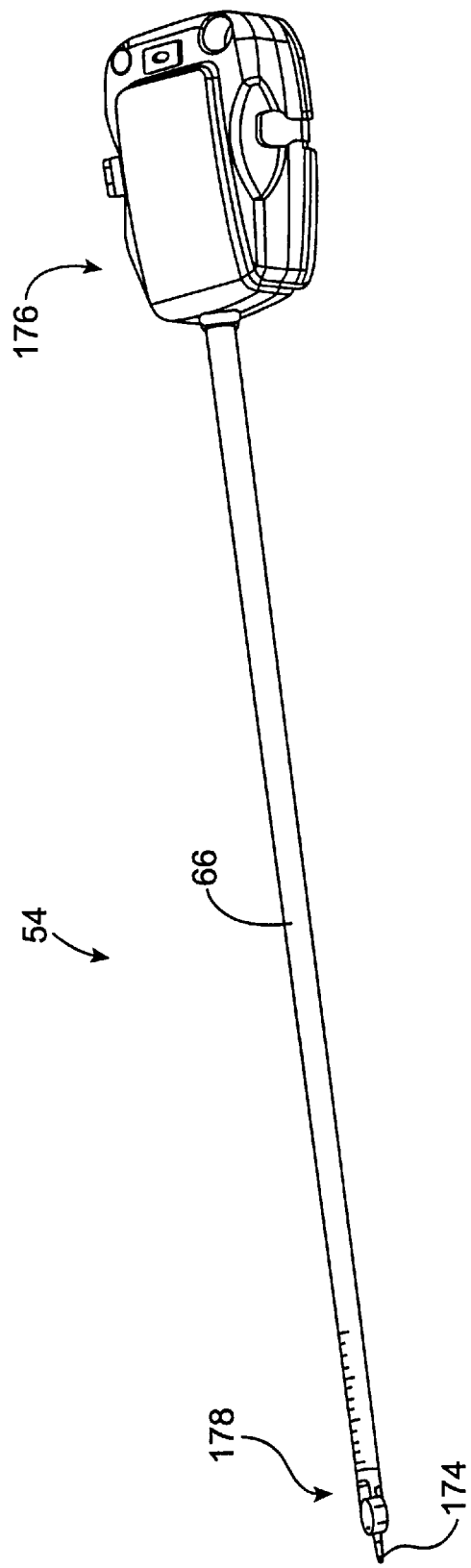
FIG. 11 is a perspective view of an exemplary articulated surgical instrument for use in the system of FIG. 1.

An exemplary articulated endoscopic surgical instrument 54 is illustrated in FIG. 11. Instrument 54 includes an elongate shaft 66 supporting an end effector 174 relative to a proximal housing 176. Proximal housing 176 is adapted for releasably mounting instrument 54 to a manipulator, and for transmitting drive signals and/or motion between the manipulator and end effector 174. As described above, a wrist 178 may provide two degrees of freedom of motion between end effector 174 and shaft 66, and the shaft may be rotatable relative to proximal housing 176 so as to provide the end effector with three substantially orientational degrees of freedom within the patient P body. Preferably, the shaft 172, wrist 178, and one or both members of end effector 174 of instrument 54 may include visible distance markings along their outer surfaces (see FIG. 11), such as in millimeters or portions of inches. Such markings aid a surgeon to understand the distances involved at the surgical site while performing remote telesurgery. The surgeon may use the information provided by the ruler markings on the instrument, for example, to gauge the proximity of his/her instruments to various organs or tissue portions, the proximity of the instruments to one another, and the size of various features of the surgical site. Such information may prove valuable when the surgical site is magnified, in 2-D or 3-D, to the point where it may be difficult for the surgeon to relate the magnified image to real scale. Additionally, the operator's console might be arranged with an information "pop-up" capability, with the surgeon being able to call up, when desired, information such as a virtual ruler simply by pushing a button, for example, or activating any other appropriate input device such as voice control. The ruler preferably would be moveable on the viewing screen using a mouse, for example, so that the surgeon could then measure a distance of interest using said virtual ruler. A variety of exemplary tools are more fully described in co-pending Provisional U.S. Patent Application Ser. No. 60/116,844 filed on Jan. 22, 1999, the full disclosure of which is incorporated herein by reference.

A number of refinements may be included in the positioning linkages to expedite and facilitate pre-positioning the manipulators in preparation for surgery. For example, it may be desirable to drive the manipulators to a position at which they support their associated surgical instruments near a center of travel of the manipulator while the positioning linkages are being moved into a proper position and orientation for surgery. This will help insure that the assistant A aligns the manipulators with the internal surgical site near the center of travel of the manipulators, thereby avoiding interruptions of the surgical procedure when the movement of the tool is inhibited by a limit of travel of the manipulator.

In some embodiments, it may be beneficial to actively drive one or more of the joints of a positioning linkage. For example, processor 152 of workstation 150 may actively drive at least one (and possibly all) of the joints of the positioning linkages to a pre-determined "nominal" configuration, so as to support each manipulator at a position and/or orientation appropriate for a surgical procedure. The processor might optionally drive the positioning linkages to selectively different pre-determined nominal configurations for differing surgical procedures so as to expedite the set-up process, for example, moving the manipulators to position the surgical instruments and endoscope for a typical coronary bypass grafting in response to a first input from operator O, or for a Nissen Fundoplication in response to an alternative input from the operator O. The assistant A may then optionally move the positioning linkages from the nominal configuration slightly as desired for a procedure on a particular patient P. After a procedure is complete, actively driving the positioning linkages clear of the patient P and/or to a cart storage/transportation configuration (with the manipulators tucked in low along side column 80) can enhance the overall number of procedures which might be performed by the robotic system in a given time.

To further aid in positioning the manipulators for surgery, the optionally releasably attached cannula 72 may be inscribed on its outer surface with markings (see FIG. 2B). Such markings may extend along the entire length of the cannula, or begin at the point along its length corresponding to the remote center of motion 64. These markings, which may comprise, for example, the distance markings on a ruler, aid a surgeon's assistant in placing the cannula so that the remote center of motion of the manipulator roughly corresponds to the center of the depth of necessary incision in the patient's body to permit insertion of the cannula. For coronary surgery, for example, the markings would permit easier placement of the center of motion at the midpoint of the depth of the incision between the patient's ribs. Such markings also permit an assistant to realize how far a cannula has been inserted into a patient's body.

A variety of alternative means for guiding positioning linkages 56, 56' to one or more nominal configurations might be provided. Referring again to FIG. 5, a joint of positioning linkage 56 is shown having nominal positioning indicators 180 and 182. To pre-configure cart 50 to a nominal configuration for a first procedure, first nominal position indicators 180 are aligned on one or more of the rotational joints 84 and sliding joints 82. A second set of nominal position indicators 182 might be brought into alignment by moving the manipulator so as to configure a cart for a different procedure. The various sets of nominal position indicators may be differentiated by color, graphics, alpha-numeric markings, or the like. Still further alternatives are possible, including software which actuates the brakes of the positioning linkages when each joint is moved into a desired position, so that moving the manipulator arm generally towards the correct orientation will, one-by-one, lock the joints into the desired nominal position. Final positioning may then be effected by gently oscillating the manipulator about the joints of the positioning linkage in any remaining degrees of freedom until the sensors indicate that the desired unlocked joints are sufficiently close to the nominal configuration so as to actuate the brakes.

The cart systems of the present invention can incorporate a number of advantageous features and structures. It is generally preferred to orient the first degree of the positioning linkages extending from a fixable base in a vertical orientation, particularly when movement about the first degree of freedom is counterbalanced. Each consecutive positioning link may be smaller and lighter from the base toward the manipulator, as clearly illustrated in FIG. 5, due to the reduced moment arm of forces applied against the manipulator. Preferably, the positioning linkage members will be designed so as to support forces against the manipulator with substantially equal contributions to the stiffness of the link structure. A particularly advantageous design approach is to initially assume that a plurality of the major structural elements of the positioning linkages, typically including the joint, axles, hubs, links and/or bearings, contribute substantially equal amounts to the total deflection when the positioning linkage is configured for surgery. In this way, no single member is over-designed in a way which increases its weight unnecessarily, and thereby avoiding a system of structural members whose overall stiffness is predominantly limited by the most compliant members. Many of the components of positioning linkages described above are commercially available from a wide variety of vendors, for example, tapered roller bearings, electrically releasable brakes, and the like.

While the exemplary embodiments of the present invention have been described in some detail by way of example and for clarity of understanding, a number of adaptations, modifications, and changes will be obvious to those of skill in the art. For example, although this invention has been described with reference to a preferred remote center of motion apparatus embodiment, the scope of the inventions described herein should not be so limited, as would be obvious to one of skill in the art. While the preferred embodiment disclosed herein has multiple robotic arms mounted to a common base 80, other arrangements of robotic arms having positioning linkages fall within the scope of this invention. For example, in another embodiment of the invention, each of the robotic surgical arms is mounted to the ceiling of an operating room. The attachment points on the ceiling may need to be reinforced to bear the weight of the robotic arms, depending upon their weight. The operating room may be dedicated to robotic surgery, or have other uses, in which case the arms may be retracted out of the normal operating space by repositioning the positioning linkages. Alternatively, the arms may be releasably attached to the ceiling, and may be detached after an operation for storage elsewhere or for maintenance. In order to accurately position the arms relative to one another, the attachment points on the ceiling will preferably be known relative to one another. With that information and the information from the sensor array along each arm, the positions of the end effectors can be accurately calculated and manipulated at the surgical site. As a result, the present invention is limited solely by the appended claims.

What is claimed is:

1. A robotic surgery system comprising:
    a base;
    a surgical end effector; and
    a robotic linkage movably supporting the end effector relative to the base, the linkage comprising:
        a plurality of driven joints coupled to a servomechanism for moving the end effector so as to manipulate tissues;
        a plurality of releasably fixable joints for pre-configuring the linkage;
        a joint sensor system coupling the fixable joints to the servomechanism, the sensor system generating joint configuration signals; and
        a brake system coupled to the fixable joints, the brake system releasably inhibiting articulation of the fixable joints previously configured in an at least substantially fixed configuration, the brake system including a brake release actuator for releasing the fixable joints to a manually repositionable configuration in which the fixable joints can be manually articulated.

2. The robotic surgery system of claim 1, wherein the brake system is biased toward the fixed configuration.

3. The robotic surgery system of claim 1, wherein the fixable joints in the repositionable configuration articulate to accommodate manual translation of the end effector in three dimensions.

4. The robotic surgery system of claim 3, wherein the fixable joints in the repositionable configuration further articulate to accommodate manual rotation of the end effector about three axes.

5. The robotic surgery station of claim 4, further comprising a handle extending from the linkage for manual positioning of the end effector, wherein the actuator is disposed on or near the handle.

6. The robotic surgery system of claim 4, wherein the linkage comprises a plurality of rigid fixable links and a plurality of rigid driven links, the fixable links coupled together by the fixable joints, the driven links coupled together by the driven joints, wherein the fixable links are supported by the base and the driven links are supported by the fixable links.

7. The robotic surgery system of claim 1, wherein the linkage is balanced about the fixable joints.

8. A robotic surgery system comprising:
    a base;
    a surgical end effector; and
    a robotic linkage movably supporting the end effector relative to the base, the linkage comprising:
        a plurality of driven joints coupled to a servomechanism for moving the end effector so as to manipulate tissues;
        plurality of releasably fixable joints for pre-configuring the linkage, wherein the linkage is balanced about the fixable joints, the fixable joints including at least two rotational joints accommodating pivotal motion about vertical axes and a vertical sliding joint accommodating translation along the vertical axes, the vertical slide supporting the rotational joints;
        a slide counterweight supported by the base; and
        a joint sensor system coupling the fixable joints to the servomechanism, the sensor system generating joint configuration signals.

9. The robotic surgery system of claim 1, wherein the robotic linkage comprises a parallelogram arrangement constraining a rigid shaft to rotation about a point along the shaft, and wherein actuation of the fixable joints moves the pivot point and the shaft.

10. The robotic surgery system of claim 1, wherein the joint sensor system transmits the joint configuration signals to a computer of the servomechanism.

11. The robotic surgery system of claim 10, wherein the computer calculates a coordinate system transformation between a reference coordinate system affixed relative to the base and the end effector using the joint configuration signals.

12. The robotic surgery system of claim 11, further comprising a plurality of robotic linkages, each linkage including a plurality of joints coupled to the sensor system and supporting an associated end effector, wherein the computer calculates coordinate system transformations between the reference coordinate system and each of the end effectors using the joint configuration signals.

13. The robotic surgery system of claim 12, wherein the joint configuration signals vary with an absolute position of the joint.

14. A support structure for supporting a first robotic surgical manipulator relative to a second robotic surgical manipulator, each surgical manipulator coupled to a servomechanism so as to robotically manipulate tissues of a patient body with a surgical end effector, the support structure comprising:
    a base coupled to the first manipulator;
    a manipulator support movably supporting the second manipulator relative to the base;
    an articulated linkage having a plurality of joints coupling the base to the manipulator support so as to allow manual movement of the second manipulator relative to the base;
    a brake system releasably inhibiting movement of the joints, wherein the brake system can release the joints supporting the second manipulator upon actuation of a single actuator; and
    a sensor system coupling the manipulator support to the servomechanism, the sensor system transmitting position signals to the servomechanism, the servomechanism calculating a position or orientation of the first manipulator relative to the second manipulator using the signals.

15. The support structure of claim 14, further comprising an articulated linkage having a plurality of joints coupling the base to the manipulator support so as to allow manual movement of the second manipulator relative to the base, and a brake system releasably inhibiting inadvertent movement of the joints, wherein the sensor system is coupled to the joints so that the position signals comprise joint configuration signals of the joints.

16. The support structure of claim 15, wherein the brake system is biased toward a locked configuration to prevent inadvertent movement of the manipulator.

17. A support structure for supporting a first robotic surgical manipulator relative to a second robotic surgical manipulator, each surgical manipulator coupled to a servomechanism so as to robotically manipulate tissues of a patient body with a surgical end effector, the support structure comprising:

a base coupled to the first manipulator;

a manipulator support movably supporting the second manipulator relative to the base;

an articulated linkage having a plurality of joints coupling the base to the manipulator support so as to allow manual movement of the second manipulator relative to the base;

a brake system biased toward a locked configuration to prevent inadvertent movement of the manipulator by releasably inhibiting inadvertent movement of the joints, wherein the brake system can release the joints supporting the second manipulator upon actuation of a single actuator;

a sensor system coupling the manipulator support to the servomechanism, the sensor system transmitting position signals to the servomechanism, the sensor system coupled to the joints so that the position signals comprise joint configuration signals of the joints, the servomechanism calculating a position or orientation of the first manipulator relative to the second manipulator using the signals.

18. The support structure of claim 17, further comprising a handle extending from the linkage adjacent the manipulator for manual positioning of the manipulator, wherein the actuator is disposed on or near the handle.

19. The support structure of claim 18, wherein the joints articulate to accommodate manual translation of the manipulator and handle in three dimensions.

20. The support structure of claim 19, wherein the joints further articulate to accommodate manual rotation of an end effector about at least one axis relative to the base and handle.

21. The support structure of claim 14, wherein the linkage is balanced about the joints.

22. The support structure of claim 14, wherein the joints include at least two rotational joints accommodating pivotal motion about vertical axes and a vertical sliding joint accommodating translation along the vertical axis, the vertical slide supporting the rotational joints, and further comprising a slide counterweight supported by the base.

23. The support structure of claim 14, further comprising a plurality of linkages, each linkage including a plurality of joints coupled to the sensor system and supporting an associated manipulator relative to the base, wherein the position signals generated by the sensor system are sufficient to define coordinate system transformations for each of the manipulator interfaces relative to a reference coordinate system of the base.

24. A minimally invasive robotic surgical system comprising an articulated robotic arm having a distal end releasably coupled to a surgical tool, said tool having an end effector and a longitudinal shaft with a distal end portion coupled to said end effector, said end effector having at least one end effector member, wherein at least one of said shaft distal end portion and said end effector member has a plurality of visual markings for determining spatial relationship.

25. The system of claim 24, further comprising an image capture device and a visual display operatively coupled to said capture device, wherein an operator viewing the visual display can visually sense at least a portion of said plurality of markings in an image of a distal portion of said surgical tool captured by said image capture device.

26. A minimally invasive robotic surgical system comprising an articulated robotic arm having a distal end coupled to an elongate structure having a length, a longitudinal bore and an outer surface, said bore for accepting an elongate shaft of a surgical tool, said elongate structure outer surface having a plurality of visual markings for determining spatial relationship, said markings useful for determining desired placement of said elongate structure in an aperture in a body wall of a patient.

27. The system of claim 26, wherein said elongate structure comprises a cannula.

28. The system of claim 26, wherein said elongate structure is releasably coupled to said distal end of said robotic arm.

29. The system of claim 26, wherein said markings comprise numbers designating the distance between certain of the markings.

30. The system of claim 26, wherein said articulated robotic arm is constructed so that a remote center of motion coincides with a portion of said length of said elongate structure, wherein said plurality of markings are useful for placing said remote center of motion of said arm substantially at the depth midpoint of said aperture.

31. The system of claim 27, wherein said aperture comprises an incision between two adjacent ribs of said patient, wherein said cannula is inserted to enable remote surgery on the heart of said patient.

* * * * *

Disclaimer

6,246,200 B1 - Steven J. Blumenkranz, Redwood City; David J. Rosa, San Jose, both of CA (US). MANIPULATOR POSITIONING LINKAGE FOR ROBOTIC SURGERY. Patent dated June 12, 2001. Disclaimer filed November 12, 2019, by the assignee, Intuitive Surgical Operations, Inc.

Hereby enters this disclaimer to the complete claims 1, 10-12 of said patent.

*(Official Gazette, May 25, 2021)*

Disclaimer

6,246,200 B1 - Steven J. Blumenkranz, Redwood City; David J. Rosa, San Jose, both of CA (US). MANIPULATOR POSITIONING LINKAGE FOR ROBOTIC SURGERY. Patent dated June 12, 2001. Disclaimer filed March 19, 2020, by the assignee, Intuitive Surgical Operations, Inc.

Hereby enters this disclaimer to the complete claims 14 and 17 of said patent.

*(Official Gazette, May 25, 2021)*